United States Patent [19]

Nesmeyanov et al.

[11] 3,996,377

[45] Dec. 7, 1976

[54] MEDICINAL PREPARATION FOR TREATING PARODONTOSIS AND METHOD OF TREATING PARODONTOSIS

[76] Inventors: Alexander Nikolaevich Nesmeyanov, Glavnoe zdanie MGU, korpus "K", kv. 105, Moscow; Ljubov Grigorievna Bogomolova, ulitsa Nekrasova, 60, kv. 131, Leningrad; Nadezhda Sergeevna Kochetkova, ulitsa Garibaldi, 23/56, korpus 4, kv. 27, Moscow; Vera Dmitrievna Vilchevskaya, ulitsa Dmitria Ulyanova, 4, korpus 2, kv. 47, Moscow; Nikanor Petrovich Palitsyn, ulitsa Stankevicha, 12, kv. 10, Moscow; Julia Julievna Gorelikova, Nagatinskaya ulitsa, 58, korpus 2, kv. 3, Moscow; Irina Gennadievna Andrianova, prospekt Smirnova, 43, kv. 27, Leningrad; Olga Petrovna Belozerova, prospekt Mira, 124, korpus 15, kv. 72; Vera Khusainovna Sjundjukova, ulitsa Vavilova, 44/2, kv. 154, both of Moscow, all of U.S.S.R.

[22] Filed: May 22, 1975

[21] Appl. No.: 579,804

Related U.S. Application Data

[63] Continuation-in-part of Ser. No. 423,533, Dec. 10, 1973, abandoned, which is a continuation of Ser. No. 119,356, Feb. 26, 1971, abandoned.

[52] U.S. Cl. ............................................. 424/295
[51] Int. Cl.$^2$ ..................................... A61K 31/295
[58] Field of Search .................................. 424/295

[56] References Cited

UNITED STATES PATENTS

| 3,035,978 | 5/1962 | Jones et al. | 424/295 |
| 3,099,699 | 7/1963 | Leigh | 424/295 |

OTHER PUBLICATIONS

Derwent Publication Abstracting, USSR, 179,309 published 8/1966.

Merck Manual, 12th Edition, (1972) pp. 255-257, 952, 968-972.

Stedman's Medical Dictionary, 21st Edition, (1969), pp. 1158, 1181 and 1205.

Goodman et al., The Pharmacological Basis of Therapeutics, (1966) pp. 1403-1406.

Primary Examiner—Norman A. Drezin
Attorney, Agent, or Firm—Haseltine, Lake & Waters

[57] ABSTRACT

A medicinal preparation for treating parodontosis comprises an active principle ingredient, viz., the sodium salt of o-carboxybenzoylferrocene, combined with a pharmaceutical filler for tablets.

The proposed method of treating parodontosis comprises oral administration of tablets, each, containing from 0.1 to 0.3 g of the active principle ingredient, viz., the sodium salt of o-carboxybenzoylferrocene, 2 or 3 times a day for 20 to 30 days.

2 Claims, No Drawings

MEDICINAL PREPARATION FOR TREATING PARODONTOSIS AND METHOD OF TREATING PARODONTOSIS

This application is a continuation-in-part of Ser. No. 423,533 filed Dec. 10, 1973 which was a continuation application of Ser. No. 119,356 filed Feb. 26, 1971, both now abandoned.

The present invention relates to a novel medicinal preparation for treating parodontosis and to a method of treating parodontosis.

The medicinal preparation for treating parodontosis in accordance with the invention comprises an active principle ingredient, viz., the sodium salt of o-carboxybenzoylferrocene, combined with a pharmaceutical filler.

The proposed preparation is employed in cases of *Parodontosis dystrophica* complicated by *Parodontitis superficialis* and *Parodontitis profunda*.

It is known in the art to treat parodontosis by use of a variety of general roborants heightening the natural resistive power of the organism combined with non-specific biological stimulants (injections of the aloe extract; oral administration of metacil, etc.). This treatment is preceded by oral cavity assanation and accompanied by massive antiphlogistic, desensitizing and local tissue metabolism stimulating therapy.

The proposed medicinal preparation has been found to stimulate the activity of certain groups of enzymes taking part in tissue metabolism.

The method of treating human parodontosis in accordance with the invention includes oral administration of tablets, each containing 0.1 to 0.3 g of the active principle, viz. the sodium salt of o-carboxybenzoylferrocene, 2 or 3 times a day for 20 to 30 days.

If the parodontal tissues show an inflammatory process, said tablets are preferably combined with curettage and epluchage of the oral cavity with compounds selected from the group consisting of antiseptics, enzymes, antibiotics and corticosteroids. The antiseptics used are a 1:5.000 aqueous solution of Furacilin, a 0.25-percent aqueous solution of chloroamine and a 3-percent aqueous solution of hydrogen peroxide. The enzymes used are a 0.1-percent aqueous solution of trypsin, 0.5-percent aqueous solution of chymotrypsin, a 0.1-percent aqueous solution of ribonuclease. The preferred antibiotics are those of the tetracycline series. The preferred corticosteroid is 17-hydroxycorticosterone.

The preparation and method of treatment of this invention have been tested under clinical conditions for 5 years on 100 patients suffering from *Parodontosis dystrophica* of differing severity. Prior to therapy, all the patients were subjected to a clinical examination which included a clinical blood test, a blood-sugar test, a general urine test and a blood serum iron test. None of the patients had hypochromic iron-deficiency anemia or an abnormal level of blood serum iron. Then the patients were broken down into three groups depending on the severity of the disease. The 1st group was made up of 12 patients suffering from 1st-degree *Parodontosis dystrophica* complicated by *Gingivitis marginalis*, characterized by denudation of the tooth roots by up to one-third of their length, incessant gingival stomatorrhagia, gingival itching and halitosis, but no tooth mobility. All patients of this group had been earlier subjected to 2 or 3 courses of comprehensive antiparodontosis therapy which included assanation of the oral cavity, tartar removal, elimination of granulations, local antiphlogistic treatment by use of a wide spectrum of antiseptic mouthwashes combined with balneological and physiotherapeutic procedures, such as hydromassage of the gums, and injection of a 10 to 20-percent solution of calcium chloride, a 5-percent solution of ascorbic acid, colanchoe juice or aloe extract into the mucosa of the gingival borders. Wherever necessary, the occlusion surface of the dental arch had been leveled off. Simultaneously the patients had been given general roborants and stimulants of the natural resistive power of the organism plus non-specific biological stimulants (injections of the aloe extract, administration per os of metacil, etc.). In spite of such an intensive treatment, the remission in this group had lasted for only 3 to 4 months, making it imperative for the patients to visit the dentist 3 or 4 times a year. The proposed preparation comprising 0.1 to 0.3 g of the active principle ingredient, viz., the sodium salt of o-carboxybenzoylferrocene, was prescribed to this group in the following regimen: 2 or 3 times a day after meals chased with water for 20 to 30 days. The patients were observed from the 3rd till the 10th day of the course of treatment to determine the side effect of the preparation as well as the human response to it. On the 10th day, the patients' state improved, the stomatorrhagia diminished, the bad halitosis was gone. On completion of the prescribed course of treatment, a repeated examination was carried out to determine the state of the mucous capillaries of the gingival border. All the patients showed capillary stability which was back almost to normal; stomatorrhagia and itching of the gums were gone. The sustained therapeutic effect lasted for 6 to 24 months. 6 months after the treatment, two patients were subjected to a repeated course with the use of the proposed preparation, after which the sustained effect lasted for 1.5 to 3 years. 1.5 to 3 years after the original course of treatment, the patients were again examined and, where necessary, a repeated course of treatment with the proposed preparation was prescribed.

The second group included 53 patients suffering from 2nd-degree *Parodontosis dystrophica* complicated by *Parodontitis superficialis* and *Parodontitis profunda*, which was characterized by the following symptoms: denudation of the tooth roots by half their length; constant gingival stomatorrhagia; suppurating and pain in the gums; periodic abscess formation in the vicinity of various groups of teeth; hypersensitivity of the tooth necks. The tooth mobility was of the 1st-2nd degree. All patients of this group had been more than once treated priorly by assanation of the oral cavity, removal of the tartar, and curettage of all pathological dental-gingival pockets. A local antiphlogistic treatment with antiseptics had been given, using a 1:5.000 aqueous solution of Furacilin, a 0.25-percent aqueous solution of chloroamine or a 3-percent aqueous solution of hydrogen peroxide. Enzymes (trypsin, chymotrypsin or ribonuclease) had also been applied; these had been introduced directly into the pathological dental-gingival pockets in combination with antibiotics of the tetracycline series. Wherever necessary, corticosteroids in the form of 0.25- or 0.5-percent ointments had been locally used. In the absence of contraindications, the patients had been given a course of physiotherapy, including UHF therapy. Wherever necessary, vitamins had been given together with the most effective antibiotics against the flora of the patients' oral cavity. The most active non-specific stimulants had also been used.

However, multiple course of said treatment had failed to stabilize the process in this group of patients; the process had usually exacerbates within 2 or 3 months, forcing the patients to seek medical aid again. The proposed preparation comprising 0.1 to 0.3 g of the active principle ingredient, viz., the sodium salt of o-carboxybenzoylferrocene, was prescribed to this group of patients for oral administration 2 or 3 times a day for 20 to 30 days. The patients were observed after 3 days of therapy, to determine their tolerance of the drug, and after 20 days to determine its therapeutic effect. All the patients registered an improvement of the general state, the inflammatory manifestation in the oral cavity were dramatically reduced and suppurating stopped altogether. A 30 - day course eliminated the tooth neck hypersensitivity.

The therapeutic effect of the proposed preparation was checked in 3 to 6 months' time by examining randomly selected patients. All the patients thus examined 2 or 3 months after said course of treatment showed reduced mobility of the teeth, induration of the pathological dental-gingival pockets and absence of inflammation of the gingival borders. The sustained affect of the proposed preparation lasted for 8 to 24 months. After a repeated examination with curettage, the patients whe needed it were given a second course of treatment using the proposed preparation: after 12 months 18 patients and after 2 years 23 patients of this group for preventive purposes. All in all, in 43 cases the process was stabilized.

The third group included 35 patients suffering from 3rd-degree *Parodontosis dystrophica* complicated by *Parodontitis profunda*, characterized by denudation of the the tooth roots by two-thirds of their length, constant gingival stomatorrhagia, swelling of the gums, pathological dental-gingival pockets and suppurting as well as periodical abscess formation in the vicinity of various groups of teeth. The mobility of the teeth was of the 2nd-3rd degree.

The earlier treatment given to this group of patients duplicated that for the 2nd group, including pulling the teeth having the 3rd-degree mobility and orthopaedic treatment. After this group had undergone multiple course of said therapy without any effect, with the process exacerbating after 2 or 3 months requiring repeated medical intervention. The proposed preparation comprising 0.2 to 0.3 g of the active principle ingredient, viz., the sodium salt of o-carboxybenzoylferrocene, was prescribed for oral administration 2 or 3 times a day for 20 to 30 days. The patients were observed after 3, 20 and 30 days of treatment. The process stabilization effected by the preparation of the invention lasted for a period from 6 to 18 months. 15 patients of this group received a repeated course of treatment after 6 months, 10 patients after 1 year. 6 patients showed no beneficial effect of the preparation.

The proposed preparation is prescribed in tablet form comprising 0.1-0.3 g of the active principle ingredient, viz., the sodium salt of o-carboxybenzoylferrocene. In accordance with the invention, the tablet filler is starch or confectioner's sugar. The medicinal preparation of this invention is prepared by any known method.

The active principle ingredient of the proposed preparation, viz., the sodium salt of o-carboxybenzoylferrocene, is preferably produced by the following route.

An apparatus equipped with a heating jacket, a reflux condenser and a stirrer is charged with phthalic anhydride and absolute ethanol, and the resultant mixture is heated with stirring at the alcohol boiling point until all phthalic anhydride has been completely dissolved. Then the heating is continued for another 30 minutes and the alcohol residue is distilled off in vacuum at a temperature not exceeding 50° C.

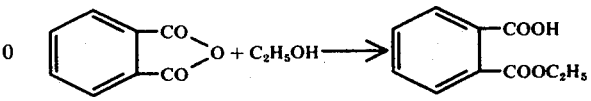

Then thionyl chloride is added by small portions to the resultant residue:

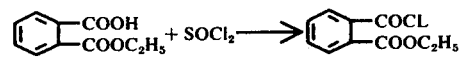

The reaction mixture thus obtained is heated for an hour at a temperature of 35° C and stirred.

The excess thionyl chloride and the by-products of the reaction are distilled off in vacuum at a temperature not exceeding 50° C. To the obtained monoethyl o-phthalate chloride is added methylene chloride as solvent and ferrocene with stirring, and passing an inert gas.

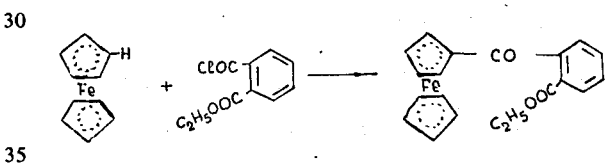

A suspension of aluminum chloride in dry methylene chloride or in higher ethers, e.g., n-dibutyl ether, is added by portions to the reaction mixture, whereupon the latter is heated at a temperature of 40° – 45° C for 4 - 5 hours with stirring. Then the reaction mass is cooled to 10° – 15° C and cool water acidified with hydrochloric acid is added thereto. Thereupon, the organic layer is separated, washed with water and the solvent is distilled off. Sodium hydroxide is added to the resultant residue, viz., ethyl ester of o-carboxybenzoylferrocene, and the mixture is heated at a temperature of 95° – 98° C.

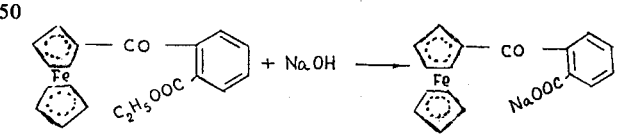

The product sodium salt of o-carboxybenzoylferrocene is filtered at a temperature of 80° C for separating the tarry products. The filtrate is cooled and a crystalline salt is separated which is then purified by re-crystallization from the minimum amount of water.

In order to obtain a purer end product, said filtrate can be cooled and then acidified with hydrochloric acid and the o-carboxybenzoylferrocene can be separated and heated with sodium hydroxide to prepare the sodium salt of o-carboxybenzoylferrocene which is employed as the active principle ingredient of the proposed medicinal preparation for treating parodontosis.

The proposed preparation is prescribed in the form of tablets comprising 0.1 – 0.3 g of the active principle ingredient, which are to be taken after or during meals chasing them with water. Application of acidic preparations (hydrochloric acid, ascorbic acid, gastric juice, etc.) prior to and following the administration of the proposed preparation in tablet form is not required, so that the preparation is easily tolerated by patients suffering from inflammatory processes in the oral cavity as well as from gastro-intestinal diseases. The preparation is not to be prescribed to patients with more than 84 hemoglobin units in their blood.

What is claimed is:
1. A method of treating parodontosis in a human having said condition comprising oral administration of an effective amount of tablets each containing from 0.1 – 0.3 g of the sodium salt of o-carboxybenzoylferrocene.
2. The method of claim 1 wherein said tablets are administered 2 to 3 times a day for 20 to 30 days.

* * * * *